United States Patent
Payton et al.

(10) Patent No.: US 10,098,874 B2
(45) Date of Patent: Oct. 16, 2018

(54) TEMOZOLOMIDE POWDER FORMULATION

(71) Applicant: AmpliPharm Pharmaceuticals, LLC, Johns Creek, GA (US)

(72) Inventors: Gary Payton, Johns Creek, GA (US); Jeff Bryant, Johns Creek, GA (US)

(73) Assignee: AMPLIPHARM PHARMCEUTICALS, LLC, Johns Creek, GA (US)

( * ) Notice: Subject to any disclaimer, the term of this patent is extended or adjusted under 35 U.S.C. 154(b) by 0 days.

(21) Appl. No.: 15/581,677

(22) Filed: Apr. 28, 2017

(65) Prior Publication Data

US 2017/0312272 A1  Nov. 2, 2017

Related U.S. Application Data

(60) Provisional application No. 62/328,929, filed on Apr. 28, 2016.

(51) Int. Cl.
| | | |
|---|---|---|
| *A61K 31/495* | (2006.01) | |
| *A61K 47/10* | (2017.01) | |
| *A61K 47/02* | (2006.01) | |
| *A61K 9/14* | (2006.01) | |
| *A61K 9/16* | (2006.01) | |
| *A61K 9/00* | (2006.01) | |

(52) U.S. Cl.
CPC .......... *A61K 31/495* (2013.01); *A61K 9/0053* (2013.01); *A61K 9/0095* (2013.01); *A61K 9/14* (2013.01); *A61K 9/1635* (2013.01); *A61K 47/02* (2013.01); *A61K 47/10* (2013.01)

(58) Field of Classification Search
CPC .. A61K 31/495; A61K 31/4188; A61K 47/14; A61K 9/14
See application file for complete search history.

(56) References Cited

U.S. PATENT DOCUMENTS

| | | | |
|---|---|---|---|
| 5,441,175 A | 8/1995 | Jacobsen et al. | |
| 5,622,721 A * | 4/1997 | Dansereau | A61K 9/2846 424/463 |
| 2001/0006650 A1* | 7/2001 | Burnside | A61K 9/1617 424/400 |
| 2005/0096365 A1 | 5/2005 | Fikstad et al. | |
| 2008/0142554 A1 | 6/2008 | Lafferty | |
| 2008/0171084 A1 | 7/2008 | Vanderbist et al. | |
| 2009/0012184 A1 | 1/2009 | Rosenberg et al. | |
| 2010/0297194 A1 | 11/2010 | Catron et al. | |

FOREIGN PATENT DOCUMENTS

| | | |
|---|---|---|
| EP | 2939662 | 11/2015 |
| EP | 2939662 A1 * | 11/2015 |
| KR | 1020100060462 | 6/2010 |

OTHER PUBLICATIONS

International Search Report issued in PCT/US2017/030112 dated Aug. 4, 2017.
International Search Report and Written Opinion issued in PCT/US2017/066824 dated Apr. 9, 2018.

* cited by examiner

*Primary Examiner* — Carlos A Azpuru
(74) *Attorney, Agent, or Firm* — Blank Rome LLP

(57) ABSTRACT

The present invention relates to a solid pharmaceutical composition of temozolomide that has good and consistent flowability as a powder and taste masking and is readily dispersible in an aqueous solution suitable for oral administration, e.g., as a dry sprinkle. This permits patients and healthcare workers to accurately measure doses.

14 Claims, No Drawings

TEMOZOLOMIDE POWDER FORMULATION

This application claims the benefit of U.S. Provisional Patent Application No. 62/328,929, filed Apr. 28, 2016, which is hereby incorporated by reference.

FIELD OF THE INVENTION

The present invention relates to a solid pharmaceutical composition of temozolomide that has good taste masking and consistent flowability as a powder and may be precisely and accurately orally administered, e.g., as a dry sprinkle.

BACKGROUND OF THE INVENTION

Temozolomide, an alkylating drug, is marketed in the U.S. as TEMODAR® for the treatment of adult patients with newly diagnosed glioblastoma multiforme (GBM) concomitantly with radiotherapy and then as maintenance treatment. Temozolomide is also marketed for the treatment of refractory anaplastic astrocytoma patients who have experienced disease progression on a drug regimen containing nitrosourea and procarbazine. Temozolomide is currently available in the form of oral capsules and a vial for injection.

A typical regimen for patients with GBM taking temozomide consists of two phases, a concomitant phase followed by a maintenance phase, both of which are weight-based dosing regimens. During the concomitant phase, the patient receives an oral administration of 75 mg/m$^2$ of temozolomide daily for 42 days concomitant with focal radiotherapy (60 Gy administered in 30 fractions). This corresponds to approximately 140 mg for a patient having a body surface area (BSA) between 1.8 and 1.9 m$^2$. Four weeks after completing the concomitant phase, the patient receives 6 cycles of maintenance treatment. In the first maintenance cycle, temozolomide is administered at 150 mg/m$^2$ (approximately 280 mg for a patient having a BSA between 1.8 and 1.9 m$^2$) once daily for five days followed by 23 days without treatment. The dosage may be escalated to 200 mg/m$^2$ (approximately 360 mg for a patient having a BSA between 1.8 and 1.9 ml) for the first 5 days of each subsequent cycle. Weight-based dosing using oral tablets and capsules is complex, and inadvertent overdose can be fatal. Capsules and tablets only come in discrete amounts, often requiring patients to self-administer various combinations of different dosage strengths of a medicine to obtain the desired dose. Temodar capsules, for instance, are available in six dosage strengths (5, 20, 100, 140, 180 and 250 mg). In many circumstances, doctors have to round the dose to fit the capsule strengths available. These factors result in a high risk for dispensing errors and administration errors, which have resulted in deaths in the past. One study found that 47% of medication errors were patient and care-giver administration errors, while 29% were dispensing errors. See, e.g., Letarte et al., *J. Neurooncol.*, 120(1), 111-1155, 2014 (analyzing reported medication errors involving oral capsules of temozolomide).

Many weight-based dosed medications avoid the need to combine various dosage strengths of a medicine by providing them as oral or intravenous liquids. Intravenous liquids are inconvenient and undesirable for self-administration. Oral liquid forms of temozolomide are undesirable as temozolomide is dangerous on skin contact, being classified for both skin corrosion/irritation and eye irritation in category 2.

There is therefore a need for convenient, safe, and reliable methods for titrating and dosing of temozolomide.

SUMMARY OF THE INVENTION

The presently claimed invention provides a temozolomide formulation that can be titrated readily and accurately. The formulation has good and consistent flowability, good taste, and good dissolution in acidic medium. Furthermore, the formulation does not readily clump.

One embodiment is a solid pharmaceutical composition that is readily dispersible in an aqueous solution suitable for oral administration. The composition comprises:

(a) granules of temozolomide and one or more emulsifiers, the granules coated with a pH dependent coating composition comprising a pH dependent coating material; and (b) a dispersant, wherein at least 80% of the solid pharmaceutical composition dissolves within 30 minutes when tested according to USP I dissolution test (basket) in 900 mL of 0.1 N HCl at 37° C.±0.5° C. and a speed of 100 rpm. The granules may further comprise an adsorbent. The coating composition may also further comprise one or more of glidants, plasticizers, or any combination of any of the foregoing. The composition may further comprise (as extragranular components) one or more of sweeteners, glidants, lubricants, flavours, or any combination of any of the foregoing.

Yet another embodiment is a temozolomide powder that is readily dispersible in an aqueous medium. The powder comprises:

(a) granules comprising (i) from about 50 to about 75% by weight of temozolimide, (ii) from about 25 to about 50% by weight of emulsifier, and (iii) optionally, from about 0.1 to about 2.5% of adsorbent, where the weight percentages are based on the total weight of the uncoated granules;

(b) a coating composition on the granules comprising (i) from about 40 to about 80% by weight of a pH-dependent coating material, (ii) from about 20 to about 60% by weight of glidant, and (iii) from about 0.1 to about 8% by weight of plasticizer, where the weight percentages for the coating composition are based on the total weight of the coating composition;

(d) from about 50 to about 75% by weight of dispersant, based on the total weight of the powder;

(e) optionally, one or more of sweeteners, glidants, lubricants, flavours, or any combination of any of the foregoing based upon 100% total weight of the temozolimide powder.

Yet another embodiment is a method of preparing a solid pharmaceutical composition of temozolomide that is readily dispersible in an aqueous solution suitable for oral administration. The method comprises:

(a) preparing granules of temozolomide and one or more emulsifiers, (b) coating the granules coated with a pH dependent coating composition comprising a pH dependent coating material; and (c) mixing the coated granules with a dispersant and optionally other excipients, wherein at least 80% of the solid pharmaceutical composition dissolves within 30 minutes when tested according to USP I dissolution test (basket) in 900 mL of 0.1 N HCl at 37° C.±0.5° C. and a speed of 100 rpm. In a preferred embodiment, step (b) includes drying the coating for a sufficient time and at a sufficient temperature to render the coating porous to water. In a preferred embodiment, step (b) further includes drying the coated granules for a sufficient time and at a sufficient temperature to render the coating porous to water. For example, the coated granules can be dried at about 25 to about 40° C., such as about 30 to about 40° C. or at about 40° C., for about 5 to about 10 minutes, to remove any residual solvent from the coating and cause cracks or pores to form in the coating. The granules in step (a) may further comprise an adsorbent. The coating composition in step (b) may further comprise one or more of glidants, plasticizers, or any combination of any of the foregoing. Step (c) may further include mixing with the coated granules one or more of sweeteners, glidants, lubricants, flavours, or any combination of any of the foregoing.

Yet another embodiment is a method of treating a proliferative disorder in a patient by administering to the patient a solid pharmaceutical composition or temozolomide powder of the present invention. The proliferative disorder can be, for example, a glioma, melanoma, a lung cancer, a lymphoma, a head and neck cancer, ovarian cancer, colorectal and/or colon cancer or esophageal cancer, or other solid tumor or hematologic malignancy. In one embodiment, the proliferative disorder is GBM. In one embodiment, an effective amount of the solid pharmaceutical composition or temozolomide powder is orally administered to treat the proliferative disorder. The desired amount to be administered may be determined by the use of a measuring device, such as a measuring cup or measuring spoon. The solid pharmaceutical composition or temozolomide powder may be administered concomitantly with radiotherapy.

DETAILED DESCRIPTION OF THE INVENTION

The presently claimed invention provides a temozolomide formulation that can be titrated readily and accurately. The formulation has good and consistent flowability, good taste, and good dissolution in acidic medium. Furthermore, the formulation does not readily clump.

All references to the U.S. Pharmacopeia are to the 39$^{th}$ edition unless otherwise indicated.

Granules

The granules are prepared by mixing the temozolomide with one or more emulsifiers and optionally one or more adsorbents. Temozolomide is 3,4-dihydro-3-methyl-4-oxoimidazo [5,1-d]-as-tetrazine-8-carboxamide (see U.S. Pat. No. 5,260,291) and can be prepared by methods known in the art.

Suitable emulsifiers include, but are not limited to, sodium lauryl sulfate, poloxamer, saturated polyglycolized glyceride (so-called Gelucire), labrasol, polysorbates (such as polyoxyethylene sorbitan monolaurate (Tween 20), polyoxyethylene sorbitan monopalmitate (Tween 40), polyoxyethylene sorbitan monostearate (Tween 60) and polyoxyethylene sorbitan monooleate (Tween 80)), sorbitan esters (such as sorbitan monolaurate (Span 20), sorbitan monopalmitate (Span 40), sorbitan monostearate (Span 60), sorbitan monooleate (Span 80), sorbitan trilaurate (Span 25), sorbitan trioleate (Span 85) and sorbitan tristearate (Span 65)), cremophor (e.g., Cremophor EL), PEG-60 hydrogenated castor oil, PEG-40 hydrogenated castor oil, sodium lauryl glutamate, disodium cocoamphodiacetate, Tyloxapol, Labrafil M2130CS, Labrafil M1944CS, Labrafil M2125CS, Capryol 90, Capryol PGMC, Lauroglycol 90, Lauroglycol FCC, Plurol Oleique CC 497, Labrafac Lipophile WL 1349, Labrafac PG, Transcutol, Compritol HD5 ATO, Compritol 888 Pellets, Biogapress Vegetal BM297ATO, Compritol E ATO, Geloil SC, Transcutol V, Triton X-100, and sodium deoxycholate. A preferred emulsifier is stearoyl macrogol-32 glycerides (available as Gelucire 50/13 from Gattefosse of Paramus, N.J.). In one preferred embodiment, the emulsifier self-emulsifies on contact with an aqueous medium forming a fine dispersion, such as a microemulsion (SMEDDS).

The weight ratio of temozolomide to emulsifier(s) may range from about 1:1 to about 3:1, such as from about 1:1 to about 2:1 or from about 2:1 to about 3:1. In one embodiment, the solid pharmaceutical composition includes (a) from about 5 to about 30% by weight of temozolimide, and (b) from about 5 to about 30% by weight of emulsifier, based upon 100% total weight of the solid pharmaceutical composition.

Suitable adsorbents include, but are not limited to, talc, fumed silica, colloidal silicon dioxide, calcium silicate, microcrystalline cellulose, and aluminum magnesium metasilicate. A preferred adsorbent is colloidal silicon dioxide. In one embodiment, the amount of adsorbent present in the uncoated granules ranges from about 0.5 to 4%, such as from about 1 to about 2%, based upon the weight of the uncoated granules. In another embodiment, the amount of adsorbent present in the uncoated granules ranges from about 0.1 to about 1%, such as from about 0.2 to about 0.8%, based upon 100% total weight of the solid pharmaceutical composition.

In one embodiment, the granules comprise (i) from about 50 to about 75% by weight of temozolimide, (ii) from about 25 to about 50% by weight of emulsifier, and (iii) optionally, from about 0.1 to about 2.5 or 4% of adsorbent, where the weight percentages are based on the total weight of the uncoated granules. In another embodiment, the granules comprise (i) from about 55 to about 70% by weight of temozolimide, (ii) from about 30 to about 45% by weight of emulsifier, and (iii) optionally, from about 0.1 to about 2.5 or 4% of adsorbent, where the weight percentages are based on the total weight of the uncoated granules. In yet another embodiment, the granules comprise about 1 to about 3% by weight of adsorbent, where the weight percentages are based on the total weight of the uncoated granules.

The granules can be prepared by melting the emulsifier (e.g., stearoyl macrogol-32 glycerides) (e.g., at 50° C.), adding the temozolomide and mixing to uniformity while maintaining the heat, allowing the mixture to harden, optionally breaking the mixture into smaller pieces (e.g., using a high shear granulator and then a jet mill), and granulating the mixture, optionally with one or more adsorbents.

Coating

The granules are coated to provide taste masking, safety in case the granules spill, and the desired release profile upon oral administration. In one embodiment, the coating composition includes a pH dependent coating material. The coating composition is preferably porous so the temozolimide can be dissolved in aqueous medium.

The pH-dependent coating material dissolves when there is a decrease in pH, and result in the release of the temozolomide. The pH dependent coating material preferably is released at a pH below about 5. In one embodiment, the pH dependent coating material is released at a pH below about 4.5. In another embodiment, the pH dependent coating material is released at a pH below about 4. Applicants surprising discovered that the pH-dependent coating dissolves in aqueous medium having a pH greater than 5 (e.g., water), such as water having a pH of about 6.8 to about 7.5. The coating provides a barrier permitting safe handling of the composition and preventing a patient or caregiver from the toxic effects of skin contact of temozolomide in the event of a spill.

Suitable pH dependent coating materials include, but are not limited to, methacrylate-based polymers, such as cationic polymers with a dimethylaminoethyl ammonium group (e.g., Eudragit® E PO available from Evonik Industries of Darmstadt, Germany). A preferred pH dependent coating material is amino methacrylate copolymer (e.g., Eudragit® E 100 available from Evonik Industries of Darmstadt, Germany). The pH dependent coating material can be a pH sensitive cationic coating material, such as polyvinylacetal diethylaminoacetate (AEA), acrylamide, aminoethyl methacrylate, N,N'-dimethylaminomethylacrylamide, N,N'-dimethylaminoethyl methacrylate, N,N'-dimethylaminopropyl methacrylate, N,N'-diethylaminoethyl methacrylate, diallyldimethylammonium chloride, and cationic polymers from natural sources (such as polylysine, polyhistidine, and chitosan).

In one embodiment, the pH dependent coating on the coated granules is porous to water.

Preferably, the amount of the pH dependent coating material is sufficient to result in taste masking of the temozolomide yet result in a desirable dissolution profile. In one embodiment, the pH dependent coating material is present in the coating composition in the range of about 40% to about 80%, and more preferably in a range of about 50% to about 70% by weight of the dry coating. In another embodiment, the pH dependent coating material is present in the range of about 1% to about 10%, and more preferably in a range of about 2.5% to about 8% or about 2.5% to about 5% by weight of the solid pharmaceutical composition A coating solution can be prepared by dissolving the pH dependent coating material in a solvent, such as isopropanol, acetone, or a mixture thereof. Optionally, additional excipients, such as a glidant (such as talc) and plasticizer (such as PEG 6000), can be added to the coating solution.

Suitable glidants include, but are not limited to, talc, fumed silica, colloidal silicon dioxide, magnesium stearate, stearic acid, kaolin, and magnesium trisilicate. A preferred glidant for the coating composition is talc. In one embodiment, the glidant is present in the coating composition in the range of about 20% to about 60% by weight, where the weight percentages are based on the total weight of the (dry) coating composition. In another embodiment, the glidant is present in the coating composition in the range of about 5% to about 40%, and more preferably in a range of about 25% to about 35% by weight of the dry coating. In yet another embodiment, the glidant is present in the range of about 0.5% to about 5%, and more preferably in a range of about 1% to about 2% by weight of the solid pharmaceutical composition.

Suitable plasticizers include, but are not limited to, polyethylene glycol, propylene glycol, triacetin, liquid paraffin, diethyl phthalate, dibutyl phthalate, glycerin, lecithin, triethyl citrate, fractionated coconut oil, castor oil, and polysorbate 80. A preferred plasticizer is polyethylene glycol (PEG), for example, PEG having a molecular weight ranging from 1000 to 8000, such as PEG 6000. In one embodiment, the plasticizer is present in a range of about 0.1% to about 8%, more preferably in a range of about 1% to about 8% by weight, where the weight percentages are based on the total weight of the (dry) coating composition. In another embodiment, the plasticizer is present in a range of about 1% to about 10%, more preferably in a range of about 3% to about 8% by weight of the dry coating. In yet another embodiment, the plasticizer is present in the range of about 0.1% to about 0.8%, and more preferably in a range of about 0.2% to about 0.4% by weight of the solid pharmaceutical composition.

The coating composition can be sprayed onto the temozolomide granules, for example, using a fluidized bed granulator (using, for example, a top spray). Preferably, the spraying is performed at a temperature of about 25 to about 40° C. In one embodiment, the spray coating is performed in a fluidized bed granulator for about 0.5 to about 4 hours, such as from about 1 to about 3 hours. Preferably, the coated granules are subsequently dried for a sufficient time to remove any residual solvents and render the coating porous to water. In one embodiment, the granules are dried at about 25 to about 40° C. (such as from about 30 to about 40° C. or at about 40° C.) for about 5 to about 10 minutes (or until the solvents have been removed to specified levels). In another embodiment, the coated granules are dried until their temperature raises by about 5 to about 10° C. (such as to a temperature ranging from about 32 to about 40° C., such as from about 33 to about 38° C. (for example, as measured by a thermometer in the bottom bowl of a fluidized bed granulator (where the top spray is off during drying)). Without wishing to be bound by any particular theory, the inventors theorize that the drying step results in cracks in the coating permitting it to dissolve in water, even at an elevated pH such as pH 6.8.

Dispersant and Other Components

The final solid pharmaceutical preparation can be prepared by mixing the coated granules with one or more dispersants and optionally other components, such as sweeteners, glidants, lubricants, and flavours.

Suitable dispersants include, but are not limited to, crospovidone, Pharmasperse® 416, isomalt, maltodextrin, mannitol, maltose, sorbitol, and maltitol, One preferred dispersant is Pharmasperse® 416 (available from SPI Pharma, Inc. of Wilmington, Del.), which contains 49.3-69.3% polyol (on a dry basis) and 30.4-50.4 calcium carbonate and has a tapped density of 0.59-0.75 g/mL and a bulk density of 0.52-0.68 g/mL. In one embodiment, the amount of dispersant ranges from about 40 to about 80%, based upon the total weight of the solid pharmaceutical composition. In another embodiment, the amount of dispersant ranges from about 50 to about 75%, such as from about 60 to about 65%, based upon the total weight of the solid pharmaceutical composition.

Suitable sweeteners include, but are not limited to, sucralose, sodium saccharin, aspartame, and neutrame. The amount of sweeteners can range from about 0% to about 2%, such from about 0.1 to about 0.5%, based upon the total weight of the solid pharmaceutical composition.

Suitable glidants include, but are not limited to, talc, fumed silica, colloidal silicon dioxide, magnesium stearate, stearic acid, kaolin, and magnesium trisilicate. In one embodiment, the glidant is colloidal silicon dioxide. In one embodiment, the amount of glidant (extragranular) ranges from about 0.1 to about 2%, such as from about 0.2 to about 1%, based upon the total weight of the solid pharmaceutical composition.

Suitable lubricants include, but are not limited to, magnesium stearate. The amount of lubricants can range from about 0.1% to about 1%, such from about 0.2 to about 0.5%, based upon the total weight of the solid pharmaceutical composition.

Suitable flavours include natural and artificial powdered flavours. The amount of flavours can range from about 0% to about 4%, such from about 1 to about 3%, based upon the total weight of the solid pharmaceutical composition.

Solid Pharmaceutical Composition

In one preferred embodiment, the solid pharmaceutical composition is in the form of a powder.

In one preferred embodiment, the powder has a Hausner ratio of from about 1.00 to about 1.18, such as from about 1.00 to about 1.11.

In another preferred embodiment, the powder has a Carr index of less than 10, such as less than 8 or less than 6 (e.g., from about 3 to about 7 or from about 4 to about 6).

In yet another preferred embodiment, the powder has a Hausner ratio of from about 1.00 to about 1.18 and a Carr index of less than 8. In yet another preferred embodiment, the powder has a Hausner ratio of from about 1.00 to about 1.11 and a Carr index of less than 6 (e.g., from about 3 to about 7 or from about 4 to about 6).

In one embodiment, the powder has a $d_{50}$ of no more than 420 microns, such as no more than 400 microns. Particle size distribution measurements, such as $d_{10}$, $d_{50}$, and $d_{90}$ values are measured according to U.S. Pharmacopeia <429> ($39^{th}$ edition).

In one embodiment, the powder has a $d_{90}$ of no more than 600 microns.

In one embodiment, the powder has a $d_{10}$ of no more than 200 microns.

In one embodiment, no more than 10% of the powder has a particle size less than 50 microns. For example, in one embodiment, no more than 10% of the powder has a $d_{10}$ less than 50 microns. In another embodiment, no more than 10% of the powder has a $d_{50}$ less than 50 microns.

In a preferred embodiment, the powder has a bulk density ranging from about 0.5 to about 0.75 g/cc or from about 0.54 to about 0.75 g/cc as measured by USP <616>.

In another preferred embodiment, the powder has a tap density ranging from about 0.6 to about 0.8 g/cc or from about 0.59 to about 0.80 g/cc as measured by USP <616>.

In one embodiment, at least 80% of the composition dissolves within 30 minutes when tested according to USP I dissolution test (basket) in 900 mL of 0.1 N HCl at 37° C.±0.5° C. and a speed of 100 rpm. In another embodiment, at least 90%, 95%, 98%, or 99% of the composition dissolves within 30 minutes when tested according to USP I dissolution test (basket) in 900 mL of 0.1 N HCl at 37° C.±0.5° C. and a speed of 100 rpm.

In one embodiment, at least 80% of the composition dissolves within 15 minutes when tested according to USP I dissolution test (basket) in 900 mL of 0.1 N HCl at 37° C.±0.5° C. and a speed of 100 rpm. In another embodiment, at least 90%, 95%, 98%, or 99% of the composition dissolves within 15 minutes when tested according to USP I dissolution test (basket) in 900 mL of 0.1 N HCl at 37° C.±0.5° C. and a speed of 100 rpm.

In one embodiment, at least 80% of the composition dissolves within 30 minutes when tested according to USP I dissolution test (basket) in 900 mL of water at 37° C.±0.5° C. and a speed of 100 rpm. In another embodiment, at least 90% or 95% of the composition dissolves within 30 minutes when tested according to USP I dissolution test (basket) in 900 mL of water at 37° C.±0.5° C. and a speed of 100 rpm.

In one embodiment, at least 80% of the composition dissolves within 15 minutes when tested according to USP I dissolution test (basket) in 900 mL of water at 37° C.±0.5° C. and a speed of 100 rpm. In another embodiment, at least 90% or 95% of the composition dissolves within 15 minutes when tested according to USP I dissolution test (basket) in 900 mL of water at 37° C.±0.5° C. and a speed of 100 rpm.

In one embodiment, at least 80% of the composition dissolves within 30 minutes when tested according to USP I dissolution test (basket) in 900 mL of acetate buffer at a pH of 4.5 at 37° C.±0.5° C. and a speed of 100 rpm. In another embodiment, at least 90% or 95% of the composition dissolves within 30 minutes when tested according to USP I dissolution test (basket) in 900 mL of acetate buffer at a pH of 4.5 at 37° C.±0.5° C. and a speed of 100 rpm.

In one embodiment, at least 80% of the composition dissolves within 15 minutes when tested according to USP I dissolution test (basket) in 900 mL of acetate buffer at a pH of 4.5 at 37° C.±0.5° C. and a speed of 100 rpm. In another embodiment, at least 90% or 95% of the composition dissolves within 15 minutes when tested according to USP I dissolution test (basket) in 900 mL of acetate buffer at a pH of 4.5 at 37° C.±0.5° C. and a speed of 100 rpm.

In one embodiment, at least 80% of the composition dissolves within 30 minutes when tested according to USP I dissolution test (basket) in 900 mL of phosphate buffer at a pH of 6.8 at 37° C.±0.5° C. and a speed of 100 rpm. In another embodiment, at least 90% or 95% of the composition dissolves within 30 minutes when tested according to USP I dissolution test (basket) in 900 mL of phosphate buffer at a pH of 6.8 at 37° C.±0.5° C. and a speed of 100 rpm.

In one embodiment, at least 80% of the composition dissolves within 15 minutes when tested according to USP I dissolution test (basket) in 900 mL of phosphate buffer at a pH of 6.8 at 37° C.±0.5° C. and a speed of 100 rpm. In another embodiment, at least 90% or 95% of the composition dissolves within 15 minutes when tested according to USP I dissolution test (basket) in 900 mL of phosphate buffer at a pH of 6.8 at 37° C.±0.5° C. and a speed of 100 rpm.

Uses

The powder can be directly administered to the patient. The patient may optionally administer the powder with a separate drink of water.

Yet another embodiment is a method of treating a proliferative disorder by administering a solid pharmaceutical composition or temozolomide powder of the present invention. The proliferative disorder can be, for example, a glioma, melanoma, a lung cancer, a lymphoma, a head and neck cancer, ovarian cancer, colorectal and/or colon cancer or esophageal cancer, or other solid tumor or hematologic malignancy. In one embodiment, an effective amount of the solid pharmaceutical composition or temozolomide powder is orally administered to treat the proliferative disorder.

One embodiment is a method of treating a patient having GBM by administering the solid pharmaceutical composition or temozolomide powder of the present invention. A typical regimen for patients with GBM taking temolozomide consists of two phases, a concomitant phase followed by a maintenance phase. During the concomitant phase, the patient receives an oral administration of 75 mg/m$^2$ of temolozomide daily for 42 days concomitant with focal radiotherapy (60 Gy administered in 30 fractions). This corresponds to approximately 140 mg for a patient having a body surface area (BSA) between 1.8 and 1.9 m$^2$. Four weeks after completing the concomitant phase, the patient receives 6 cycles of maintenance treatment. In the first maintenance cycle, temozolomide is administered at 150 mg/m$^2$ (approximately 280 mg for a patient having a BSA between 1.8 and 1.9 m$^2$) once daily for five days followed by 23 days without treatment. The dosage may be escalated to 200 mg/m$^2$ (approximately 360 mg for a patient having a BSA between 1.8 and 1.9 ml) for the first 5 days of each subsequent cycle.

Packaging

The powder can be packaged in a high density polyethylene (HDPE) container (e.g., a round HDPE bottle used for pharmaceuticals). The powder can be dispensed and administered with a dosing syringe, scoop, or a cap (e.g., a cap of a bottle or jar such as one fitted with a fill-to line).

EXAMPLES

The following examples are merely illustrative of the present invention and should not be construed as limiting the scope of the invention in any way as many variations and equivalents that are encompassed by the present invention will become apparent to those skilled in the art upon reading the present disclosure.

Example 1

A powder having the formulation shown in Table 1 below was prepared as follows

TABLE 1

| Ingredient | % (w/w) | Amount per gram |
|---|---|---|
| Temozolomide | 10.00% | 100.0 mg |
| Pharmasperse 416 | 77.00% | 770.0 mg |
| Gelucire 50/13 (steroyl macrogol-32 glycerides) | 10.00% | 100.0 mg |
| Eudragit E 100 (Dimethylaminoethyl Methacrylate Copolymer) | 2.00% | 20.0 mg |
| Talc, NF | 0.85% | 8.5 mg |
| PEG 6000 | 0.15% | 1.5 mg |

The Gelucire 50/13 was heated to approximately 50° C. until liquefied. Temozolomide was added at a 1:1 ratio to the melted Gelucire. The mixture was mixed until the temozolomide was uniformly dispersed while maintaining heating at approximately 50° C. The heated dispersion was transferred to a foil-lined tray, and allowed to cool and harden. The hardened sheets of the mixture were broken apart into smaller pieces. The hardened pieces were milled using a Sturtevant SDM-2 model jet mill to a target particle size of 40-80 μm or an average of 60 μm.

A coating mixture was prepared by (i) dissolving Eudragit E 100 in a 50/50 (by weight) mixture of acetone/isopropanol (approximately 12-15% Eudragit by weight) to form a first mixture, (ii) adding talc and PEG 6000 to a separate 50/50 (by weight) mixture of acetone/isopropanol and mixing vigorously (5-7% talc by weight; 0.5-1% PEG 6000 by weight) to form a second mixture, and (iii) combining the first and second mixtures to form the coating mixture. The Eudragit E 100 coating mixture was sprayed onto the temozolomide granules using a fluid bed granulator with top-spray capability until fully coated (approximately 1-10 mg/cm$^2$ with a target of 8 mg/cm$^2$). The coated granules were dried and collected. The coated granules were combined with Pharmasperse 416 in a ratio that provides for 100 mg temozolomide per gram of powder Example 2

Oral granules (powder) having the formulation shown in Table 2 below was prepared as follows.

The Gelucire 50/13 was heated to approximately 50° C. until liquefied. Temozolomide was added to the melted Gelucire. The mixture was mixed until the temozolomide was uniformly dispersed (approximately 15 minutes) while maintaining heating at approximately 50° C. The heated dispersion was transferred to cooling trays lined with non-stick or wax paper, and allowed to cool and harden. The hardened sheets of the dispersion were broken apart into smaller pieces.

Half of the silicon dioxide was add to a high shear granulator. The hardened pieces of the dispersion were transferred to the high shear granulator. The blend was mixed with both the bottom agitator and chopper blade to reduce the particle size of the Gelucire/temozolomide dispersion and discharged. The material was processed through a jet mill to the desired particle size. The granules were added to a fluid bed coater equipped with top spray capability.

Eudragit E 100 was mixed with a 60/40 mixture of isopropanol/acetone until dissolved. Talc and PEG 6000 were added and mixed until uniform to form a suspension. The Eudragit suspension was sprayed onto the temozolomide granules with a Glatt GPCG 120 fluid bed processor equipped with a top spray (inlet air temperature of 25-40° C., outlet air temperature of 20-25° C., atomizing air pressure of 1.5-2 bar) for 2 hours. They spraying was discontinued, and the drying in the fluid bed processor continued for ~8-9 minutes, such that the temperature of the product as measured in the bottom bowl raised by 7-8° C. (indicating that the solvents had been removed).

The coated granules were added to a V-blender. Pharmasperse 416, sucralose, and flavor were added and mixed for 15-30 minutes. The second half of the colloidal silicon dioxide and magnesium stearate were added and mixed for 2 minutes. The blend was discharged from the V-blender.

TABLE 2

| Ingredient | % (w/w) | Amount per gram |
|---|---|---|
| Temozolomide | 18.0% | 180.0 mg |
| Pharmasperse 416 | 63.9% | 639.15 mg |
| Gelucire 50/13 (stearoyl macrogol-32 glycerides) | 10.0% | 100.0 mg |
| Amino methacrylate copolymer, NF (Eudragit E 100) | 2.85% | 28.5 mg |
| Talc, NF | 1.4% | 14.0 mg |
| PEG 6000, NF | 0.285% | 2.85 mg |
| Magnesium stearate, NF | 0.35% | 3.5 mg |
| Sucralose, NF | 0.2% | 2.0 mg |
| Colloidal silicon dioxide, NF | 1.0% | 10 mg |
| Natural and Artificial Powdered Flavors | 2.0% | 20.0 mg |
| Total | 100% | 1000 mg |

250 mg of the oral granules were tested by USP dissolution apparatus I (baskets) at 100 rpm in 900 mL of medium at 37° C. The dissolution test was repeated six times and the dissolution percentages averaged for each run. The test results are provided in the table below.

| Run | Medium | Percentage dissolved after 15 minutes | Percentage dissolved after 30 minutes |
|---|---|---|---|
| #1 | Water only | 90.2% | 99.9% |
| #2 | 0.1N HCl | 88.7% | 100.1% |
| #3 | Acetate, pH 4.5 | 87.3% | 99.9% |
| #4 | Phosphate buffer, pH 6.8 | 88.4% | 100.2% |

Throughout this specification, various publications are referenced. The disclosures of these publications in their entireties are hereby incorporated by reference into this application in order to more fully describe the state of the art to which the disclosed matter pertains. The references disclosed are also individually and specifically incorporated by reference herein for the material contained in them that is discussed in the sentence in which the reference is relied upon.

We claim:

1. A method of preparing a solid pharmaceutical composition of temozolomide that is readily dispersible in an aqueous solution suitable for oral administration, the method comprising:
   (a) preparing granules of temozolomide and one or more emulsifiers selected from sodium lauryl sulfate, poloxamer, saturated polyglycolized glyceride, labrasol, polysorbates, sorbitan esters, cremophor PEG-60 hydrogenated castor oil, PEG-40 hydrogenated castor oil, sodium lauryl glutamate, disodium cocoamphodiacetate, tyloxapol, lauroyl macrogol-6 glycerides, oleoyl macrogol-6 glycerides, linoleoyl macrogol-6 glycerides, propylene glycol monocaprylate, propylene glycol monocaprylate, propylene glycol monolaurate, polyglyceryl-3 dioleate, polyglyceryl-3 dioleate oleate, triglycerides medium-chain, propylene glycol dicaprylocaprate, diethylene glycol monoethyl ether, behenoyl polyoxyl-8 glycerides or PEGylated glyceryl behenate, glyceryl behenate, glyceryl dipalmitostearate, glyceryl behenate E471, diethylene glycol monoethyl ether, octylphenol ethoxylate, sodium deoxycholate, and a mixture of (i) refined soybean oil, (ii) glyceryl distearate and (iii) polyglyceryl-3 dioleate,
   (b) coating the granules with a pH dependent coating composition comprising a pH dependent coating material; and
   (c) mixing the coated granules with a dispersant and optionally other excipients,
wherein (i) at least 80% of the solid pharmaceutical composition dissolves within 30 minutes when tested according to USP I dissolution test (basket) in 900 mL of 0.1 N HCl at 37° C.±0.5° C. and a speed of 100 rpm, and (ii) the pH dependent coating is released at a pH below about 5.

2. The method of claim 1, wherein step (b) further comprises drying the coated granules for a sufficient time and at a sufficient temperature to render the coating porous to water.

3. The method of claim 1, wherein step (b) further comprises drying the coated granules at about 40° C. for about 5 to about 10 minutes.

4. The method of claim 1, wherein the emulsifier is stearoyl macrogol-32 glycerides.

5. The method of claim 1, wherein the weight ratio of temozolomide and emulsifier is from about 1:1 to about 3:1.

6. The method of claim 1, wherein the weight ratio of temozolomide and emulsifier is from about 1.5:1 to about 2:1.

7. The method of claim 1, wherein the pH dependent coating is released at a pH below about 4.5.

8. The method of claim 1, wherein the pH dependent coating is released at a pH below about 4.

9. The method of claim 1, wherein the pH dependent coating composition is porous to water.

10. The method of claim 1, wherein the pH dependent coating material comprises an amino methacrylate copolymer.

11. The method of claim 1, wherein the pH dependent coating composition further comprises a glidant and a plasticizer.

12. The method of claim 1, wherein the granules further comprise an adsorbent.

13. The method of claim 12, wherein the adsorbent is colloidal silicon dioxide.

14. The method of claim 1, wherein the composition is in the form of a powder.

* * * * *